US012788898B2

(12) United States Patent
Mills et al.

(10) Patent No.: US 12,788,898 B2
(45) Date of Patent: Nov. 10, 2026

(54) SAFETY DEVICE FOR MOUNTING ONTO A DRUG DELIVERY DEVICE

(71) Applicant: Becton, Dickinson and Company, Franklin Lakes, NJ (US)

(72) Inventors: Freddy Mills, Sinard (FR); Albert Chansavang, Grenoble (FR); Olivier Albenge, Vif (FR)

(73) Assignee: Becton, Dickinson and Company, Franklin Lakes, NJ (US)

(*) Notice: Subject to any disclaimer, the term of this patent is extended or adjusted under 35 U.S.C. 154(b) by 452 days.

(21) Appl. No.: 18/383,748

(22) Filed: Oct. 25, 2023

(65) Prior Publication Data

US 2024/0139429 A1 May 2, 2024

(30) Foreign Application Priority Data

Oct. 28, 2022 (EP) .................................... 22306635

(51) Int. Cl.
*A61M 5/32* (2006.01)

(52) U.S. Cl.
CPC .......... *A61M 5/326* (2013.01); *A61M 5/3245* (2013.01); *A61M 2005/3247* (2013.01)

(58) Field of Classification Search
CPC ................ A61M 5/3257; A61M 5/326; A61M 2005/3247; A61M 5/3245
See application file for complete search history.

(56) References Cited

U.S. PATENT DOCUMENTS

| | | | | |
|---|---|---|---|---|
| 4,935,013 | A * | 6/1990 | Haber | A61M 5/3275 604/263 |
| 6,719,731 | B2 * | 4/2004 | Parmigiani | A61M 5/3275 604/177 |
| 8,496,627 | B2 * | 7/2013 | Chelak | A61M 5/326 604/198 |
| 8,821,453 | B2 | 9/2014 | Doyle et al. | |
| 2004/0267206 | A1 | 12/2004 | Rimlinger et al. | |
| 2005/0159709 | A1 * | 7/2005 | Wilkinson | A61M 5/326 604/197 |
| 2005/0277894 | A1 | 12/2005 | Westbye et al. | |
| 2007/0191780 | A1 | 8/2007 | Modi | |
| 2008/0051724 | A1 | 2/2008 | Bedford et al. | |
| 2014/0039406 | A1 | 2/2014 | Verespej et al. | |
| 2014/0200518 | A1 | 7/2014 | Ekman et al. | |
| 2014/0213983 | A1 | 7/2014 | Ekman et al. | |
| 2020/0316311 | A1 * | 10/2020 | Holland | A61M 5/3271 |

* cited by examiner

*Primary Examiner* — Matthew F Desanto
(74) *Attorney, Agent, or Firm* — The Webb Law Firm

(57) ABSTRACT

The safety device includes a tubular body configured to receive a barrel, a head arrangement configured to abut against the flange and to lock into a flange, at least two actuation arms connecting the tubular body and the head arrangement, said actuation arms having a proximal link connected to the head arrangement by a proximal hinge and a distal link connected to the tubular body by a distal hinge, the proximal link and the distal link being connected by an intermediate hinge, the actuation arm being movable between a collapsed position in which the tubular body is maintained in a position proximally close to the flange uncovering the needle and an extended position in which the tubular body is maintained in a position distally distant from the head arrangement shielding the needle; a locking means for maintaining the actuation arms in a collapsed position and a biasing member for maintaining the actuation arms in an extended position.

20 Claims, 12 Drawing Sheets

SAFETY DEVICE FOR MOUNTING ONTO A DRUG DELIVERY DEVICE

CROSS-REFERENCE TO RELATED APPLICATION

This application claims priority to European Patent Application No. 22306635.8 filed Oct. 28, 2022, the disclosure of which is hereby incorporated by reference in its entirety.

BACKGROUND OF THE INVENTION

Field of the Invention

The present invention relates to a safety device for mounting onto a drug delivery device such as a prefilled or pre-fillable syringe in order to protect a user from needle stick injuries after injection of a medical product. The invention also relates to a drug delivery device including this safety device.

Description of Related Art

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to the safety device or drug delivery device of the invention and the "proximal direction" is to be understood as meaning the opposite direction to said direction of injection, that is to say the direction towards the user's hand.

Drug delivery devices, such as pre-fillable or prefilled syringes, usually comprise a hollow body or barrel forming a container for a medical product. This body comprises a distal end in the form of a longitudinal tip defining an axial passageway through which the medical product is expelled from the container. The distal end is equipped with a needle for injection of the medical product into an injection site.

It is of great importance that the patients and users are protected from any risk of needle stick injuries, particularly between the moment that injection is finished and the discarding of the drug delivery device.

In order to minimize the risks of needle stick injuries, drug delivery devices may be equipped with a safety device that protects the needle after injection. Safety devices usually comprise a tubular body for receiving the syringe barrel, and a needle cover, in the form of a protective sleeve, that slides relative to the tubular body. The needle cover has a retracted position in which the needle cover is substantially contained inside the tubular body to allow a user to carry out an injection, and an extended position in which the needle cover moves distally from the retracted position to cover the needle once the injection is completed.

Although known injection systems are generally satisfactory, they do not always meet all of the user's expectations and they can include a number of components. Therefore, they can be expensive to manufacture and thus this can limit the widespread use of safety devises at the expense of the security of medical users and patients.

They also tend to include components made of various materials which can be complex and expensive to recycle.

SUMMARY OF THE INVENTION

A need exists for an improved safety that provides a user with more convenient safety device that is also cost effective and easy to manufacture.

In one aspect, the invention is directed to a safety device for mounting onto a drug delivery device having a barrel including with a flange at its proximal end and an injection needle at its distal end, and a piston rod including a piston flange, the safety device including:

a tubular body extending along a longitudinal axis (A), the tubular body being configured to receive the barrel, a head arrangement configured to abut against the flange and to lock into the flange, at least two actuation arms connecting the tubular body and the head arrangement, said actuation arms having a proximal link connected to the head arrangement by a proximal hinge and a distal link connected to the tubular body by a distal hinge, the proximal link and the distal link being connected by an intermediate hinge, the actuation arm being movable between a collapsed position in which the tubular body is maintained in a position proximally close to the flange uncovering the needle and an extended position in which the tubular body is maintained in a position distally distant from the head arrangement shielding the needle, a locking means for maintaining the actuation arms in a collapsed position and a biasing member for maintaining the actuation arms in an extended position.

At least one of the hinges can be a living hinge.

The safety device can be formed in a single shot injection molding process.

The biasing element can be an element of the group having a spring blade, a torsion spring and an elastic band.

The biasing member can include one distal end secured on the tubular body and one proximal end secured on the distal link.

The distal link can include a housing configured to receive the biasing member proximal end and the tubular body includes a casing configured to receive the biasing member distal end.

The spring blade can have an opening.

The torsion spring has a helical central part and two opposite ends.

The intermediate hinge inwardly overtakes the plan defined by the proximal hinge and distal hinge when the actuation arm is in its extended position.

The head arrangement can include an annular head which includes a proximal ring and a distal ring jointed by a shoulder whereon the flange abuts.

The annular head can comprise at least one locking tab configured to axially retain the flange.

The tubular body comprises at least one leg extending in cantilever and having a catch at its free end, the leg being configured to deflect radially outward to allow the catch to slide over the annular head during mounting and to deflect radially inward after mounting completion so that the catch axially retains the tubular body relative to annular head.

The annular head can include two ramp surfaces configured to guide the legs when the legs slide on the annular head.

At least one distal link can include two longitudinal ribs having a proximal side perpendicular to the distal link and arcuate distal side.

The tubular body can include a means for securing the biasing member onto the tubular body.

The head arrangement includes a crown having a proximal plate configured and sized to lock onto the flange and a distal plate mounted on the tubular body, the proximal plate and the distal plate being connected by at least two actuation arms.

The proximal plate includes two symmetrical ribs, each ribs having two locking teeth configured to retain the flange.

The safety device can include two legs having a catch, extending in cantilever from the distal plate, configured and sized to engage into a window provided in the proximal plate and to lock into the rib.

The distal link includes a lip adjacent the intermediate hinge and the proximal link includes a ramped end adjacent the intermediate which forms a groove with the lip.

In a second aspect, the invention is directed to a drug delivery device having a barrel including with a flange at its proximal end and an injection needle at its distal end, and a piston rod including a piston flange fitted with a safety device, wherein the piston flange includes a ramped surface distally convergent configured to outwardly deflect the locking means maintaining the actuation arms in a collapsed position.

BRIEF DESCRIPTION OF THE DRAWINGS

With reference to the appended drawings, below follows a more detailed description of aspects and embodiments of the invention cited as examples.

DESCRIPTION OF THE INVENTION

Figure 1:
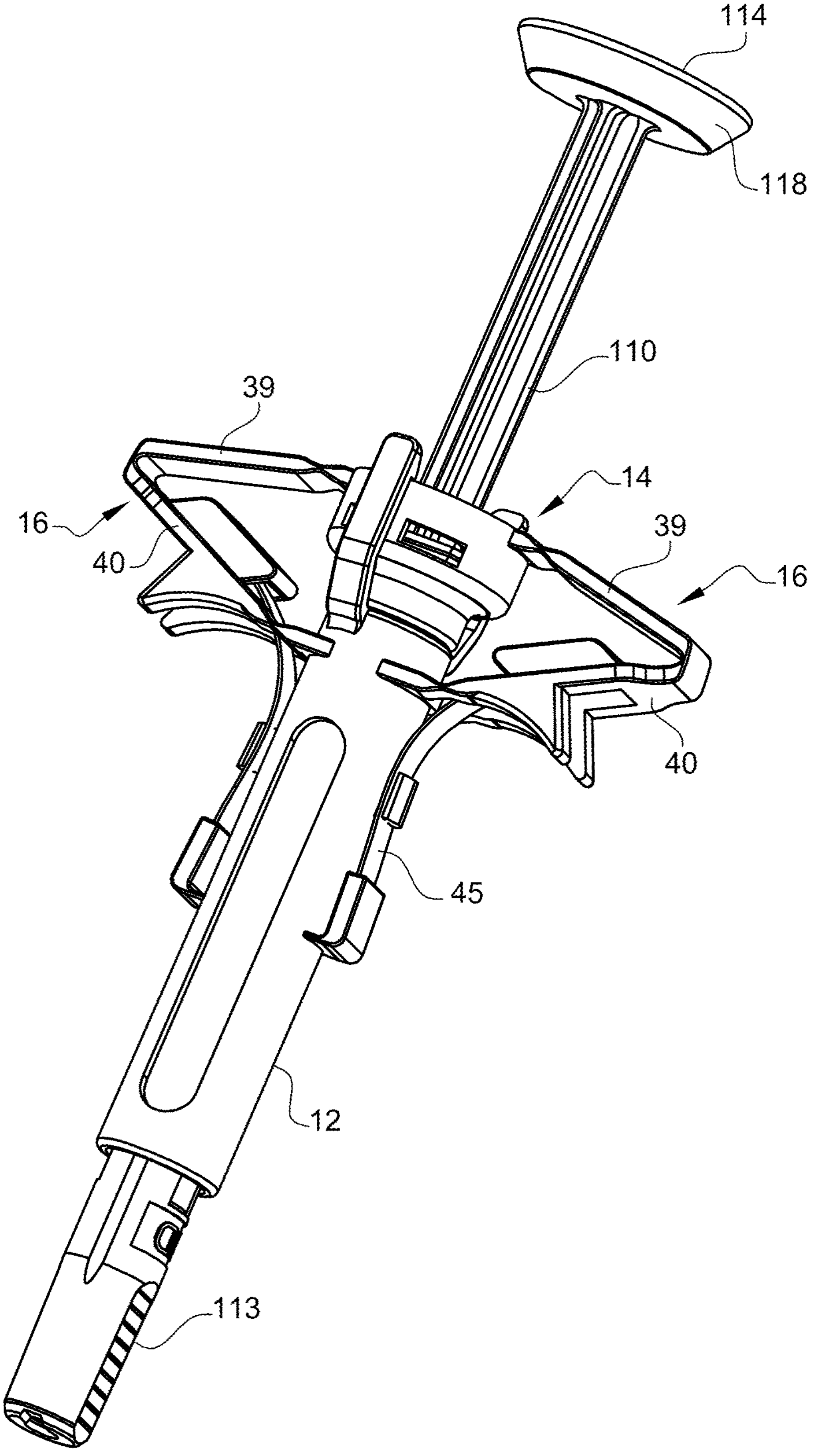
FIG. 1 is a perspective view of a safety device according to one embodiment of the invention mounted on a drug delivery device.
Figure 2:
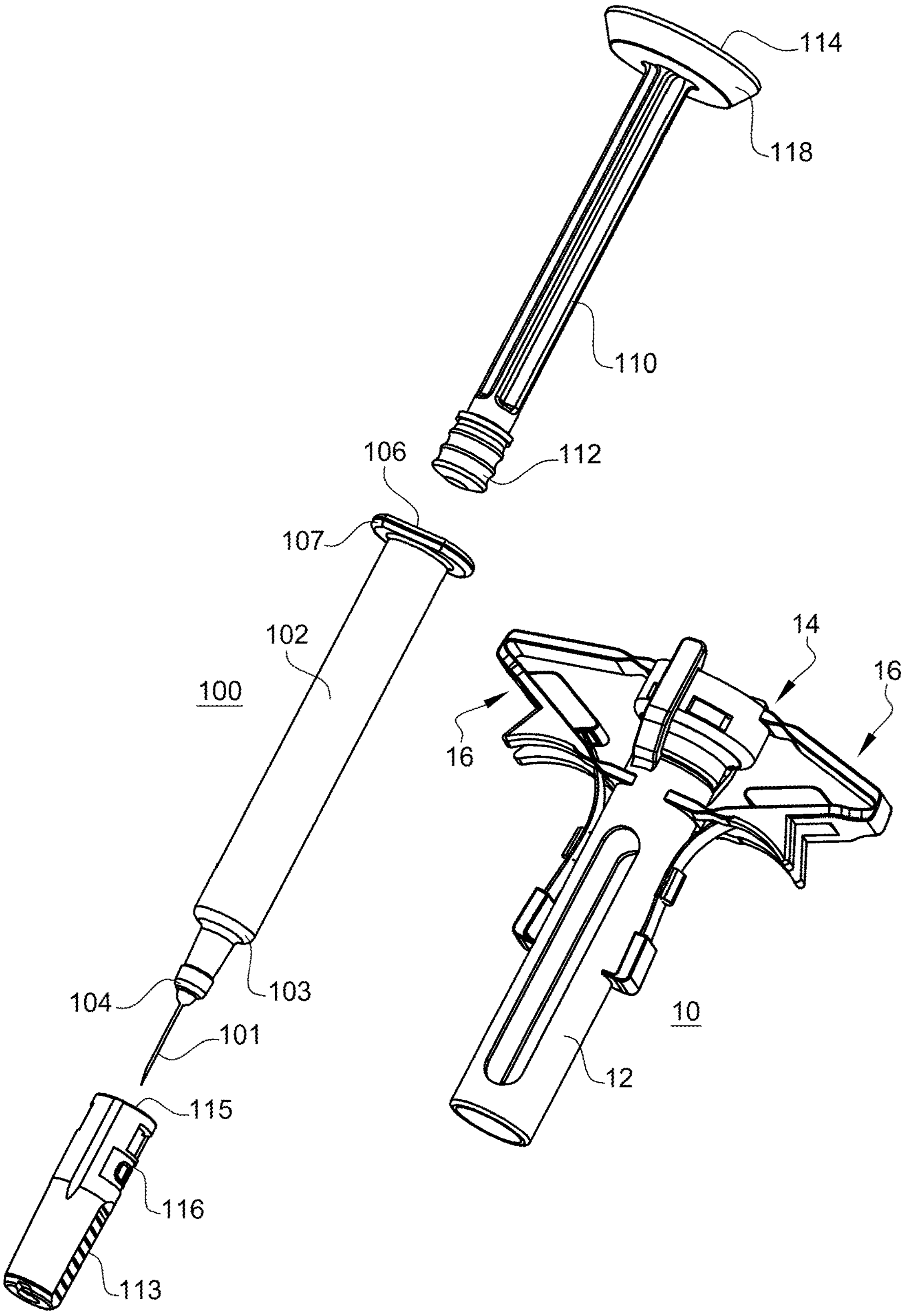
FIG. 2 is an exploded view of the safety device and of the drug delivery device of FIG. 1.

The different features of the embodiments can be used in combination with and used with other embodiments as long as the combined parts are not inconsistent with or interfere with the operation of the device and assembly. This invention is not limited in its application to the details of construction and the arrangement of components set forth in the following description or illustrated in the drawings. The embodiments herein are capable of being modified, practiced or carried out in various ways. The phraseology and terminology used herein is for the purpose of description and should not be regarded as limiting. The use of "including," "comprising," or "having" and variations thereof herein is to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not limited to physical or mechanical connections or couplings. Further, terms such as distal, proximal, up, down, bottom, and top are relative, and are to aid illustration, but are not limiting. The embodiments are not intended to be mutually exclusive so that the features of one embodiment can be combined with other embodiments as long as they do not contradict each other. Terms of degree, such as "substantially", "about" and "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely present in the structure.

With reference to the Figures, a safety device 10 is configured to be mounted onto a drug delivery device 100 to protect an injection needle 101 of the drug delivery device 100 after an injection has been carried out.

The drug delivery device 100 may be a prefilled or prefillable syringe. The drug delivery device 100 includes a tubular barrel 102 defining a reservoir for containing a medical product such as a drug. The tubular barrel 102 may be made of a plastic or of a glass material. This barrel 102 has a distal shoulder 103 provided with a distal tip 104 longitudinally protruding from said shoulder 103 along a longitudinal axis A. The distal tip 104 defines an axial passageway in fluid communication with the reservoir and is equipped with the injection needle 101 for injecting the medical product in an injection site. The barrel 102 further includes an opposite opened proximal end 106 provided with a flange 107. The opened proximal end 106 receives a plunger rod 110 for pushing a stopper 112 located inside the barrel 102 to expel the medical product from the reservoir to the injection site via the distal tip 104 and the injection needle 101.

The drug delivery device 100 may be fitted with a tip cap 113 for protecting and sealing the injection needle 101 before injection. The tip cap 113 may be comprised of a soft inner element 115 and a rigid outer element 116.

The piston rod 110 is fitted with a plunger flange 114 at its proximal end. In some embodiments, the plunger flange 114 can include a ramped surface 118. The ramped surface 118 is conically convergent toward the distal direction.

Figure 3:
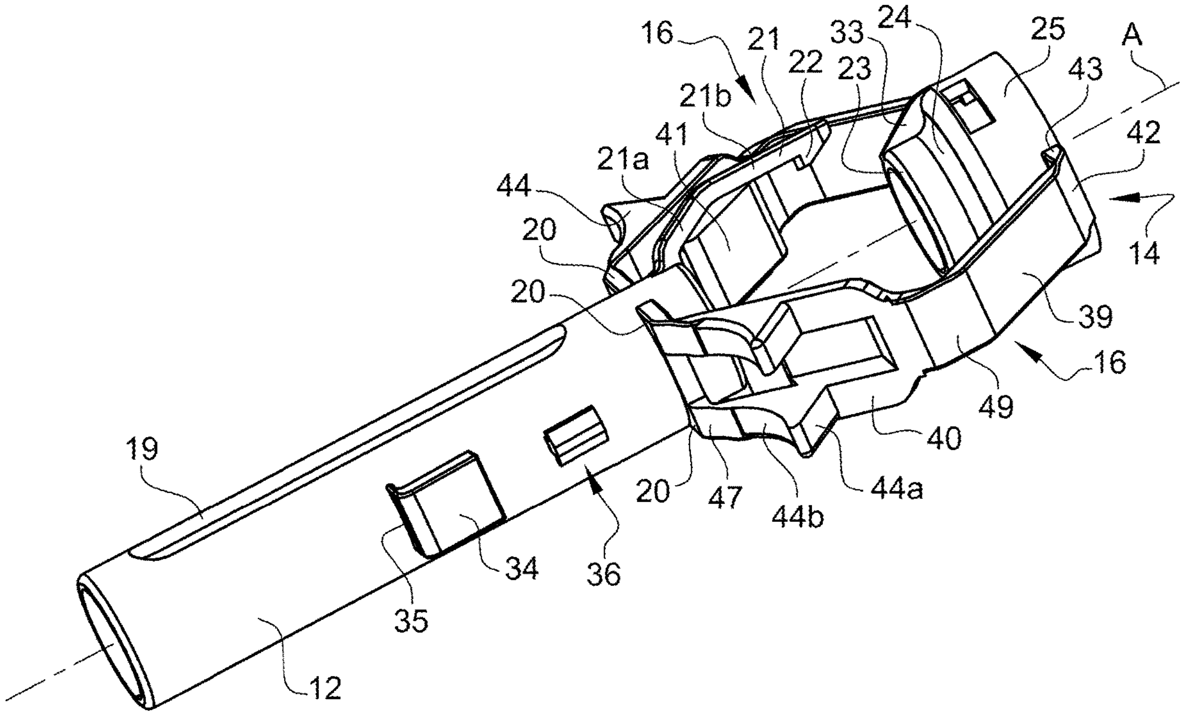
FIGS. 3 and 4 are perspective views of the safety device of FIG. 1.
Figure 4:
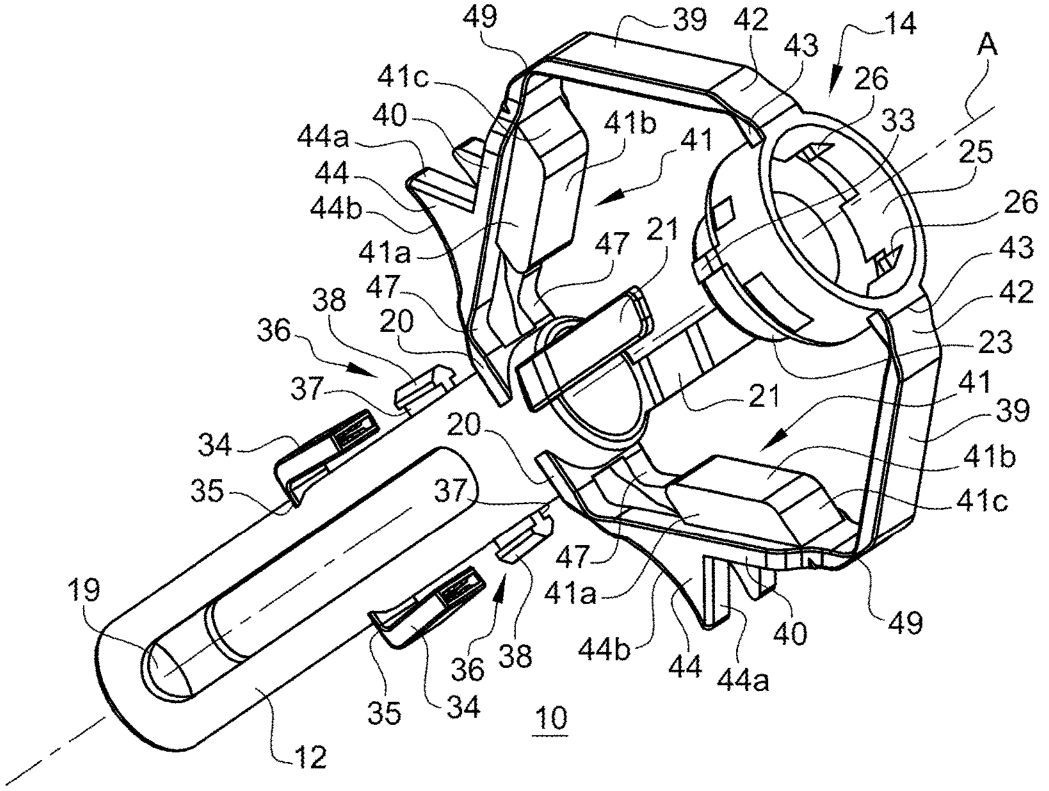
Figure 5:
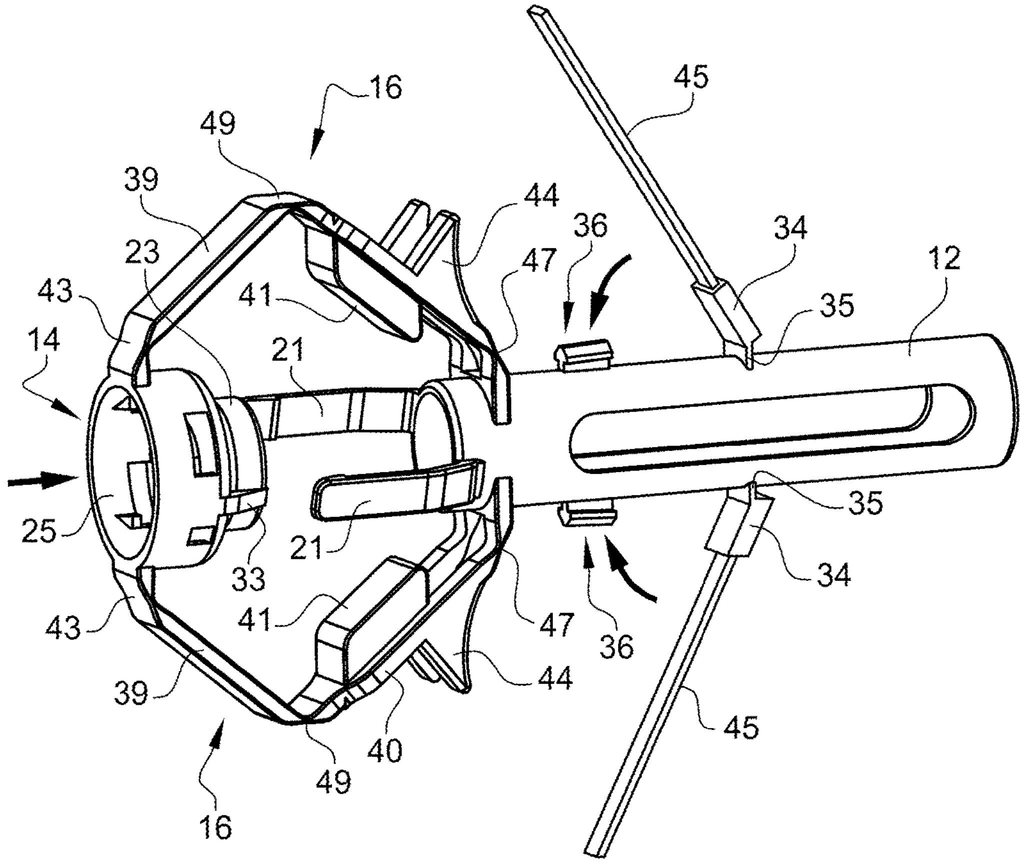
FIG. 5 is a perspective view of the safety device during its assembly.

Turning to FIG. 3 and FIG. 4, the safety device 10 includes a tubular body 12, which extends along the central longitudinal axis A and is configured and sized to engage on the barrel 102 and a head arrangement which can include an annular head 14 configured and size to engage on the barrel 102 and to lock on the flange 107.

In some embodiments, two articulated actuation arms 16 connect the tubular body 12 and the annular head 14. The actuation arms 16 are symmetrical spaced apart from each other about the central longitudinal axis A. Other embodiments may include three or four actuation arms 16. The tubular body 12 is a tubular element, which has an inner diameter sized and configured so that the tubular body 12 can axially slide relative to the barrel 102. In practice, the tubular body inner diameter slightly exceeds the external diameter of the barrel 102. In some embodiments, the tubular body 12 can be provided with one or more windows 19 so that any marking or labelling applied on the barrel 102 and so that the drug contained in the barrel 102 can be visible to a user prior to injection. In the illustrated embodiments, the tubular body 12 is provided with two windows 19 spaced apart by 180°.

In some embodiments, the tubular body 12 can comprise two pairs of tabs 20 positioned at its proximal end. Each pair of tabs 20 extends radially from the outer surface of the tubular body 12 and, the tabs 20 can be oriented substantially perpendicular to the central longitudinal axis A.

The tubular body 12 further comprises two legs 21. The legs 21 extends in cantilever from the proximal end of the tubular body 12. In some embodiments, the leg 21 can have a first radially sloped part 21*a* and a second longitudinal part 21*b* parallel to the axis A, thus radially offsetting the leg free end relative to the tubular body 12. In some embodiments, the cantilevered attachment of the legs 21 onto the tabs 20 provides the legs 21 with elastic resilience in a radial direction relative to the tubular body 12. At the end of the legs 21, is a catch 22, which is internally oriented. In some embodiments, the catch 22 has a ramped end.

The tubular body 12 can include two receiving casings 34 configured to receive the end of a biasing element, which will described in more details later. In some embodiments, the casings 34 can have a rectangular cross section. The casings 34 have an open proximal end and a closed distal end. In some embodiments, the casings 34 are connected to the tubular body 12 by a tab 35 which allows the casing 34 to elastically bend relative to the tubular casing 12 within an angular range of 0° to 45°. The tubular body 12 can further include two clips 36 located on the outer surface of tubular body 12 and substantially half-way between the casing 32 and the tabs 20. The clips 36 include a V shaped head 38 sitting on a narrowed base part 37.

Now turning to FIGS. 3 and 4, the annular head 14 comprises a distal ring 23 attached by a shoulder 24 to a proximal ring 25. The distal ring 23 is coaxial with the tubular body 12 and has an inner diameter, which substantially equates the inner diameter of the tubular body 12.

As can be seen on FIG. 4, the proximal ring 25 can be provided with one or more locking tabs 26, which radially protrude from the inner surface of said proximal ring 25. In the illustrated embodiments, the proximal ring 25 includes four locking tabs 26 spaced apart by 90°.

In the case of the four locking tabs 26 being formed, the locking tabs 26 are equally spaced from each other, or provided at a position at every 90° about the central axis A. Nonetheless, the locking tabs 26 may as well comprise three locking tabs 26, or five or more locking tabs 26.

In some embodiments, the annular head 14 is provided with two sloped ramp surfaces 33 configured to guide the legs 21. The ramped surfaces 33 are sloped toward the distal direction and connect the distal ring 23 and the proximal ring 25 as it can best seen on FIG. 3.

The annular head 14 and the tubular body 12 are linked by the two articulated actuation arm 16, which each includes a proximal link 39 and a distal link 40.

In some embodiments, each proximal link 39 has a substantially rectangular shape and is connected to a tab 43 protruding from the annular head 14 by a first proximal hinge 42.

In the illustrated embodiment, the first proximal hinge 42 is a living hinge formed by a thinning of the plastic material, which the safety device 10 is made of. This allows the proximal links 39 to rotate relative to the tabs 43.

In some embodiments, each distal link 40 has a substantially rectangular shape and is connected to two tabs 20 by a distal hinge 47 which can be a living hinge made by a thinning of the plastic material which forms the safety device 10. In the illustrated embodiments, each distal hinge 47 is separated in two parts corresponding to the two tabs 20.

In some embodiments, each distal link 40 includes a housing 41 which is positioned on its inner surface. The housing 41 has a substantially parallelepiped shape and includes two lateral walls 41*a*, a lower wall 41*b* and a proximal end wall 41*c*. As it can be seen more clearly on FIG. 3, each housing 41 is therefore open on its distal end and on its upper side. In the illustrated embodiment the proximal end 41*c* is sloped in the distal direction.

As depicted on the FIGS., each distal link 40 can further include two ribs 44. The ribs 44 are positioned on the longitudinal sides of each distal link 40. The ribs 44 include a proximal side 44*a*, which is perpendicular to the distal link 40 and a distal side 44*b*, which has an arcuate shape.

The proximal link 39 and the distal link 40 are joined by an intermediate hinge 49, which can be a living hinge made by a thinning of the plastic material which forms the safety device 10.

Thus, in some embodiments, the safety device 10 comprises two symmetrical articulated actuation arms 16 which connect the tubular body 12 and the annular ring 14 and comprises a unitary structure integrally molded of thermoplastic material.

In some embodiments, the safety device 10 can be a single piece component. Further, the safety device 10 can be formed by a single shot molding process.

In some embodiments, in an initial state, (see e.g. FIG. 3 or FIG. 4), after manufacturing by injection molding, the safety device 10 is configured in a state wherein the annular head 14 and the tubular body 12 are axially spaced apart while the proximal link 39 and the distal link 40 form a substantially right angle. In practice, the angle between proximal link 39 and the distal link 40 can be comprised between for example 75° and 105°.

When an axial force applies to the safety device 10, the actuation arms 16 may bend about the living hinges 42, 47 and 49 and flex radially outwardly or inwardly depending on the force direction. The actuation arms 16 are therefore transitionable from an initial state where the proximal link 39 and distal link 40 form a first angle—substantially right angle—to:

(i) a collapsed position where the proximal link 39 and the distal link 40 are substantially parallel to each other or at least form an acute angle, or (ii) an extended position where the proximal link 39 and the distal link 40 form are substantially in line with each other.

The safety device 10 when in its initial state of FIGS. 3 and 4, has no internal capacity to move from the collapsed state to the extended state.

The safety device 10 of the invention includes at least one biasing member. The biasing member can be made of an elastic and resilient material, which has a low creep capability so that its resilience and its elasticity are maintained even after a long term storage.

In the embodiments of FIGS. 1 to 10, the safety device 10 includes two spring blades 45 which urge the actuation arms 16 into their extended position. The spring blades 45 can be of spring steel or of any elastic material capable of returning to its original state despite significant deflection even after a long term storage.

Starting with a safety device 10 is its initial position, it can be brought into the collapsed position.

To do so, the tubular body 12 is pushed in a proximal direction so that the legs 21 which extend from said tubular body 12 deflects against the ramps 33. At the end of the push, the catch 22 locks against the free end of the proximal ring 25 achieving an appropriate retention of the tubular body 12 onto the annular ring 14 as illustrated on FIG. 6. In some embodiments, the engagement of the legs 21 on the free end of the proximal ring 25 produces an audible and/or a tactile signal indicating that locking is positively achieved.

Figure 6:
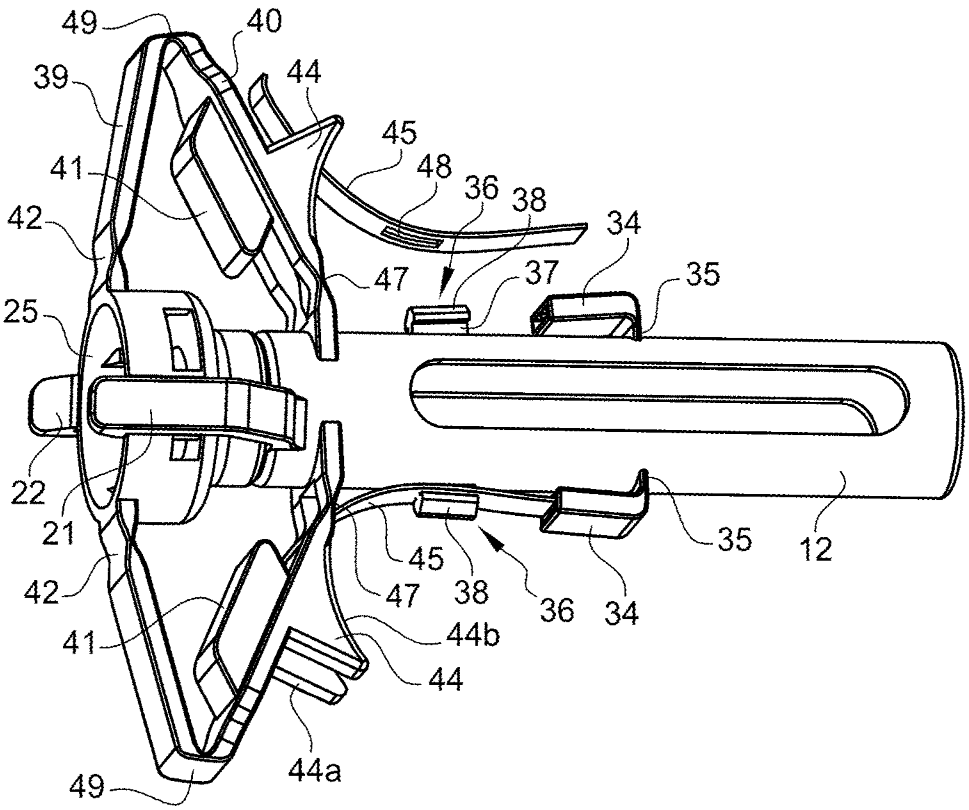
FIG. 6 safety device in a collapsed state.

In this locked state, the actuation arms 16 are pushed in a collapsed state as can be seen on FIG. 6.

In the depicted example, the spring blades 45 have an opening 48. One end of the spring blade 45 is engaged into one of the casing 34 as seen on FIG. 5. This is made easy by the fact that the casing 34 can bend about the tab 35.

With one distal end engaged into the casing 34, the spring blades 45 move toward the tubular body 12. As the spring blades 45 move closer to the tubular body, the opening 48 snaps past the clip V-shaped head 38 and locks into the narrowed base 37 thus permanently securing the spring blade 45 onto the tubular body 12. The spring blade can be secured onto the tubular body by any suitable means such as hot stamping or welding.

The proximal end of each spring blade 45 then rests in the housing 41 and applies a torque on the each distal link 40. In other words, the spring blades 45 impart a biasing force on the distal links 40 in a radial direction, which urges the actuation arm 16 into the extended position. Each spring blades 45 stores mechanical energy as they are in a bent state against the collapsed actuation arms 16.

Figure 14:
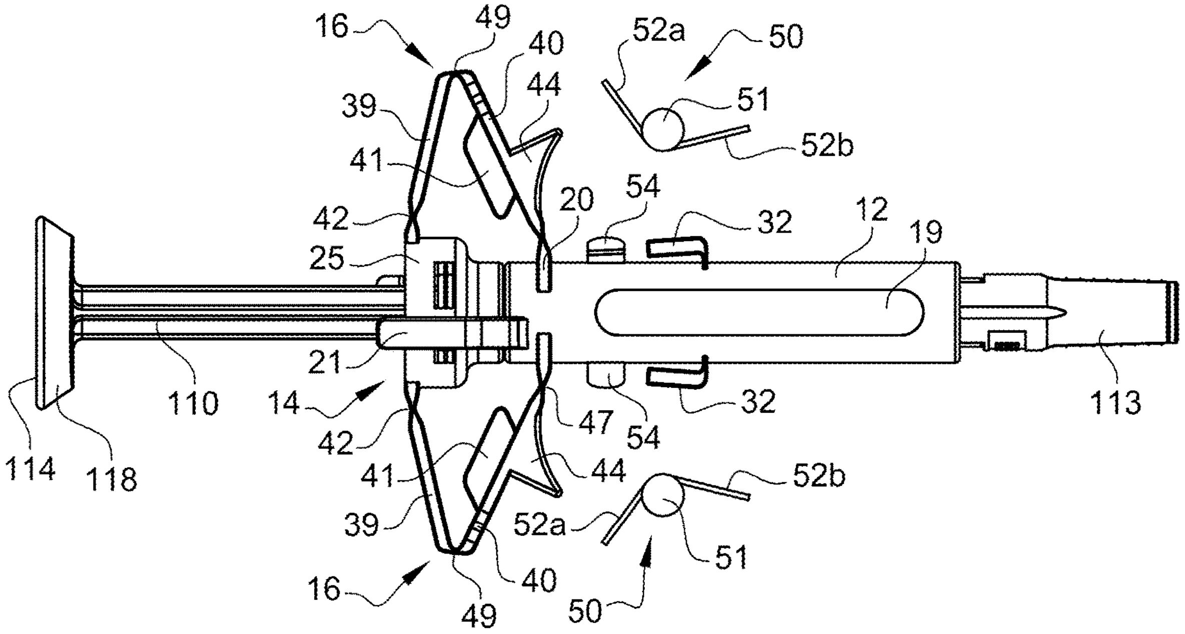
FIG. 14, FIG. 15 and FIG. 16 show another embodiment of a safety device.
Figure 15:
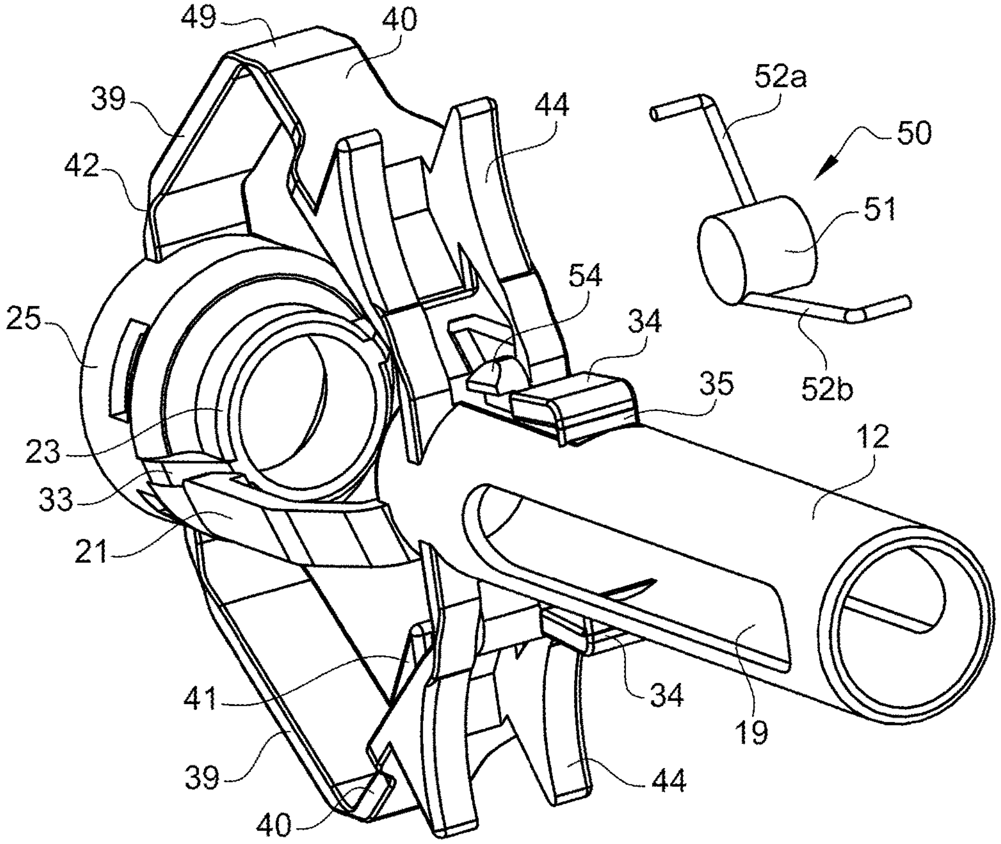
Figure 16:
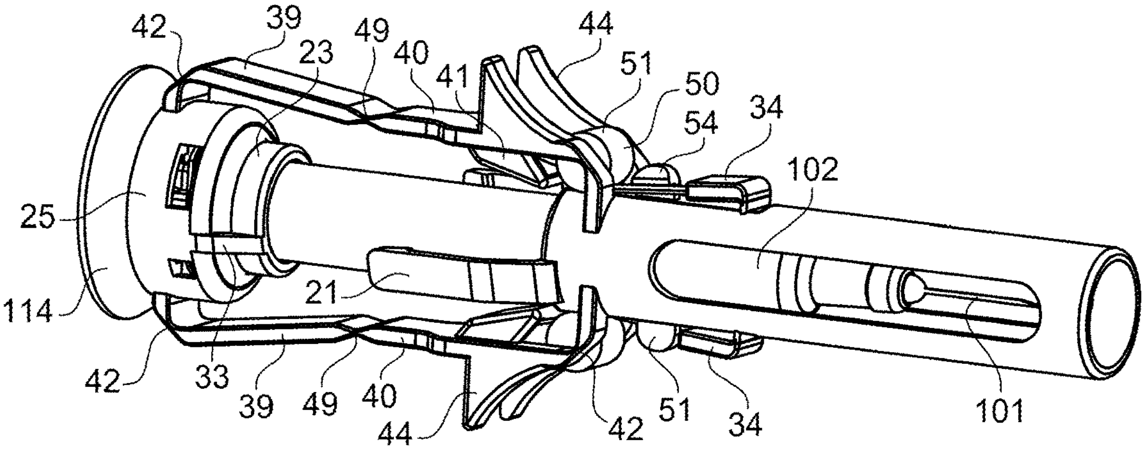

In some embodiments illustrated on FIG. 14 to 16, the biasing member comprises a torsion spring 50 having a helical central part 51 and two opposite ends 52*a*, 52*b*. In the illustrated embodiment, the torsion spring distal end 52*b* can be longer its proximal end 52*a*.

The distal end of each torsion spring 50 is engaged in a casing 34 and is clipped under the hook 54 while the distal end rests into the housing 41.

The proximal end of each torsion spring 50 then rests in the housing 41 and applies a torque on the each distal link 40. In other words, the torsion springs 50 impart a biasing force on the distal links 40 in a radial direction, which urges the actuation arm 16 into the extended position. Each torsion spring 50 store mechanical energy as they are in a twisted state.

Figure 17:
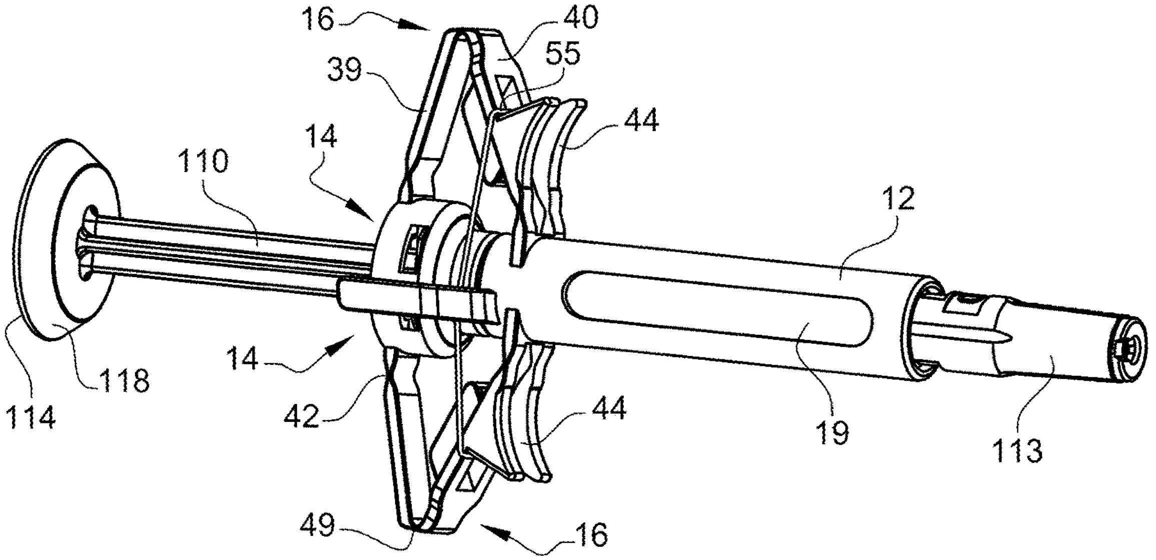
FIG. 17 and FIG. 18 show another embodiment of a safety device.
Figure 18:
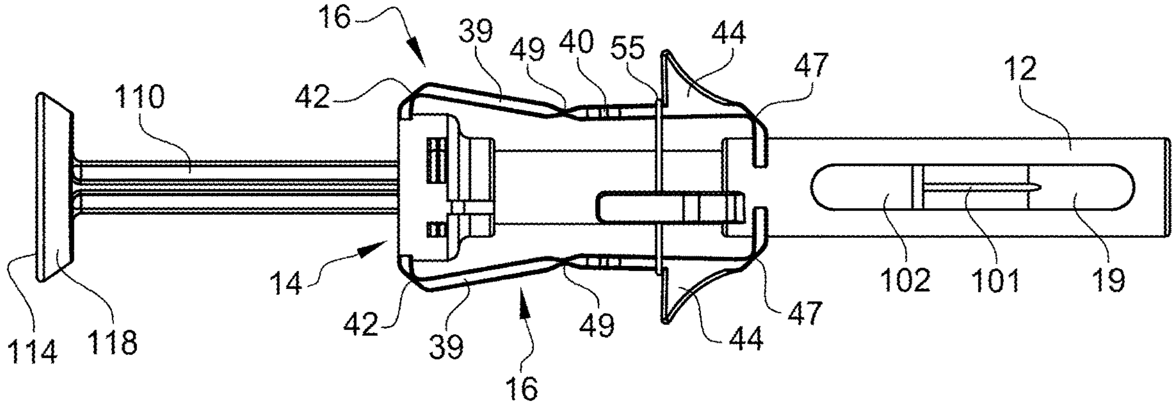

In some embodiments illustrated on FIGS. 17 and 18, the biasing member comprises an elastic band 55 arranged around the distal links 40. The elastic band 55 can be made of latex, rubber, silicone rubber, thermoplastics, thermoplastic elastomers, or other suitable elastic materials.

An it can be seen on FIG. 17 which shows the safety device in its collapsed position, the elastic band 55 stretches over the two actuation arms 16. In the illustrated embodiment of FIGS. 17 and 18, the elastic band 55 is retained by the ribs 44 and goes under the legs 21. The elastic band 55 is therefore in a stable position.

In this collapsed configuration, which includes a biasing member 45 or 50, the safety device 10 is in a stable state and can be shipped and stored for later use or can be immediately engaged on a drug delivery device.

Figure 7:
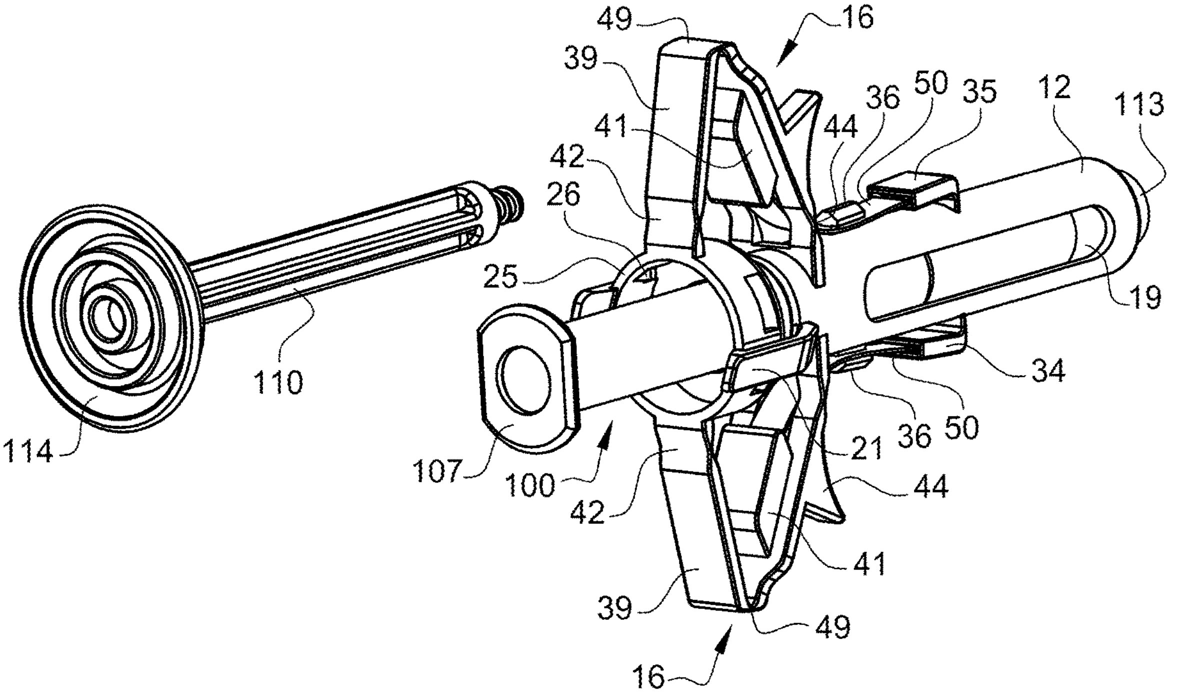
FIG. 7 shows a drug delivery device being engaged in the safety device.

In an exemplary use, the safety device 10 can be engaged on a drug delivery device 100, which can be a prefilled syringe as illustrated on FIG. 7.

The drug delivery device distal end is inserted through the annular head 14 and is pushed in a distal direction (see e.g. FIG. 7). The annular head 14 is locked onto the barrel flange 107. The locking tabs 26 deflect when the annular head 14 is pushed in a proximal direction so that the annular head 14 is retained on the barrel flange 107.

The drug delivery device 100 is axially locked on the safety device 10, however the drug delivery device 100 is free to rotate relative to the safety device 10, which can be useful as user tend to rotate any drug delivery device before injection to visually check the drug which is about to be injected.

Figure 8:
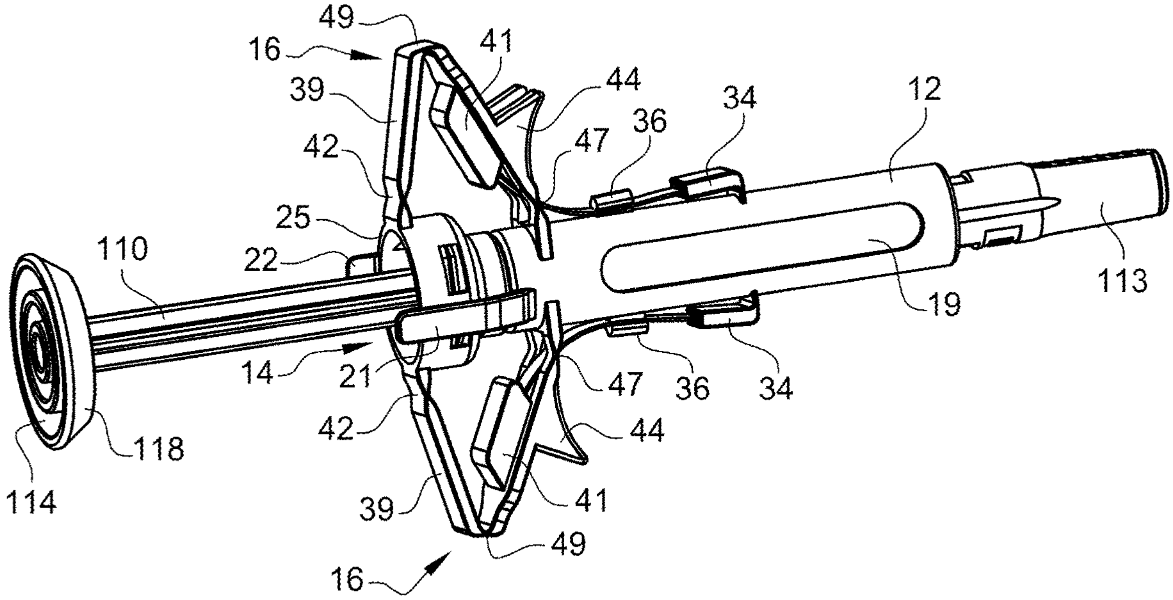
FIG. 8 shows a safety device mounted on a drug delivery device in a pre-injection position.

The drug delivery device 10 fitted with a safety device 100 as illustrated on FIG. 8 can be stored for a later use.

When an injection of the drug contained in the drug delivery device 100 is required, a user may first remove the tip cap 113.

The drug delivery device 100 is ready for injection. The user can visually check the drug through the windows 19 and can rotate the plunger rod 110.

Administering an injection with a drug delivery device fitted with the safety device 10 is substantially the same as administering an injection with a drug delivery device fitted with the safety device 10 according to the prior art and thus is not likely to confuse a user and permits a user-friendly operation.

Figure 9:
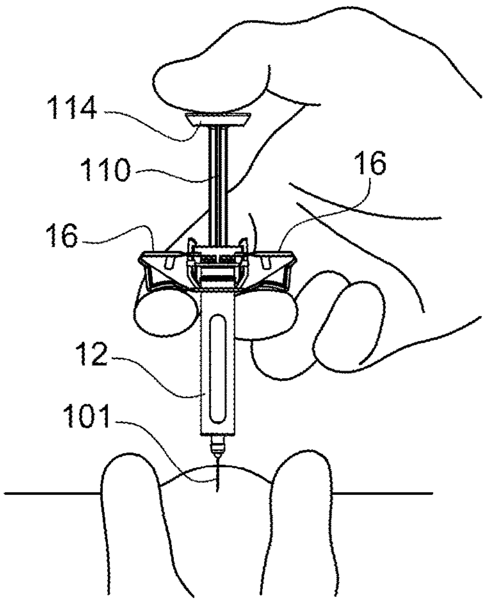
FIGS. 9 and 10 illustrate an exemplary use of a safety device mounted on a drug delivery device.

In an exemplary use illustrated on FIG. 9, the user can apply a pushing force on the piston rod flange 114 typically by applying a thumb on the piston rod flange 114 while the user maintains one finger—typically the index—on one distal link 40 and one finger—typically the middle finger—on the other distal link 40.

In this embodiments where the distal links 40 include two ribs 44, the arcuate side 44*b* provides an intuitive and ergonomic surface to place the user's fingers.

Figure 10:
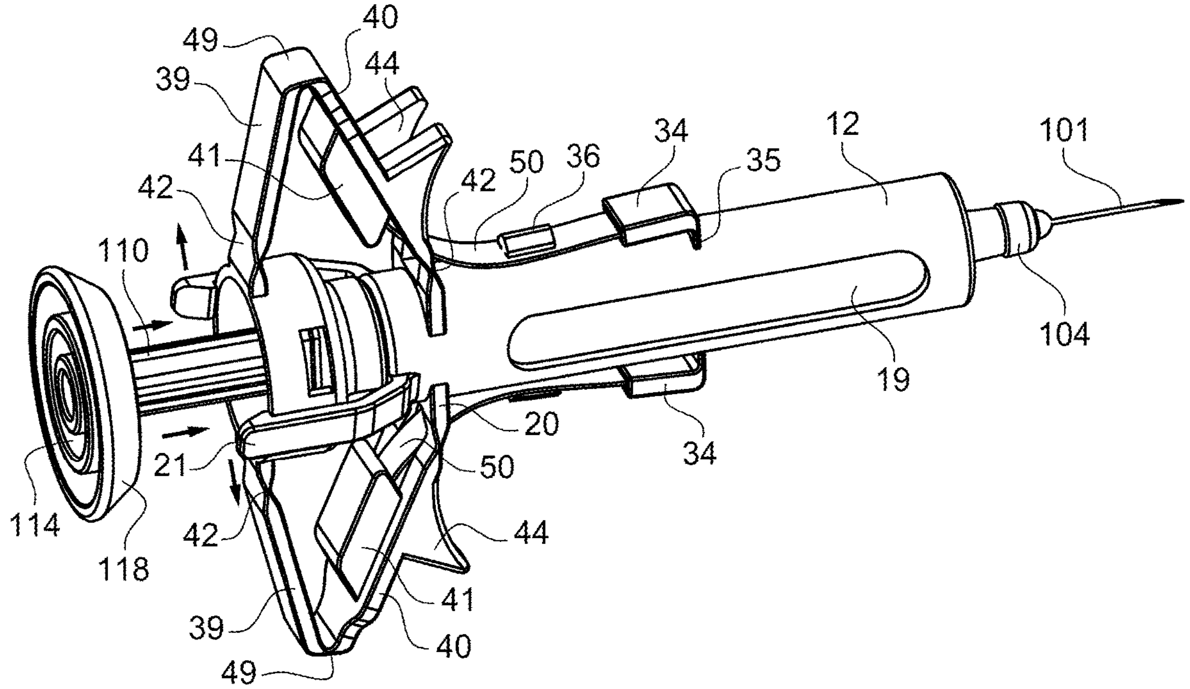

As the injection progresses, the piston rod flange 114 moves closer to the annular head 14. At the end of the injection, the piston rod flange 114 abuts against the catch 22. By further pushing the piston rod flange 114, the ramp portion 118 comes in abutment with the ramp provided in the catch 22 of each legs 21 as indicated by the arrows of FIG. 10. The legs 21 are thus forced to deflect outwardly thereby releasing the catch 22. The actuation arms 16 and the tubular body 12 are released from the annular head 14 and are therefore free to move axially along the barrel 102.

The biasing members release their mechanical energy, which they stored and apply a torque on the distal links 40, thus urging the actuation arms 16 into the extended position. In the extended position of the actuation arms 16, the tubular body 12 encapsulates the needle 101 as the tubular body 12 is pushed away from the annular head 14.

Figure 11:
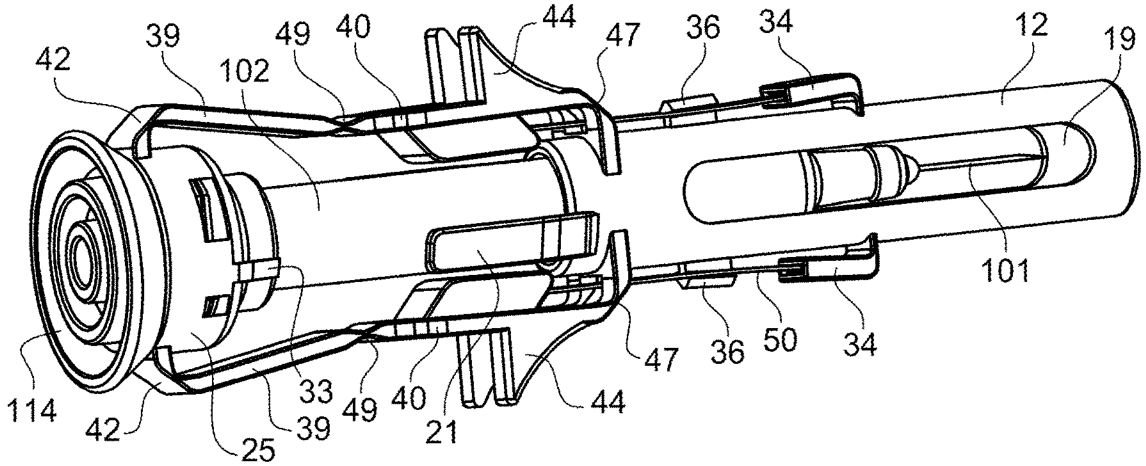
FIG. 11, FIG. 12 and FIG. 13 are perspective views according to different angles of a safety device mounted on a drug delivery device in an extended state.
Figure 12:
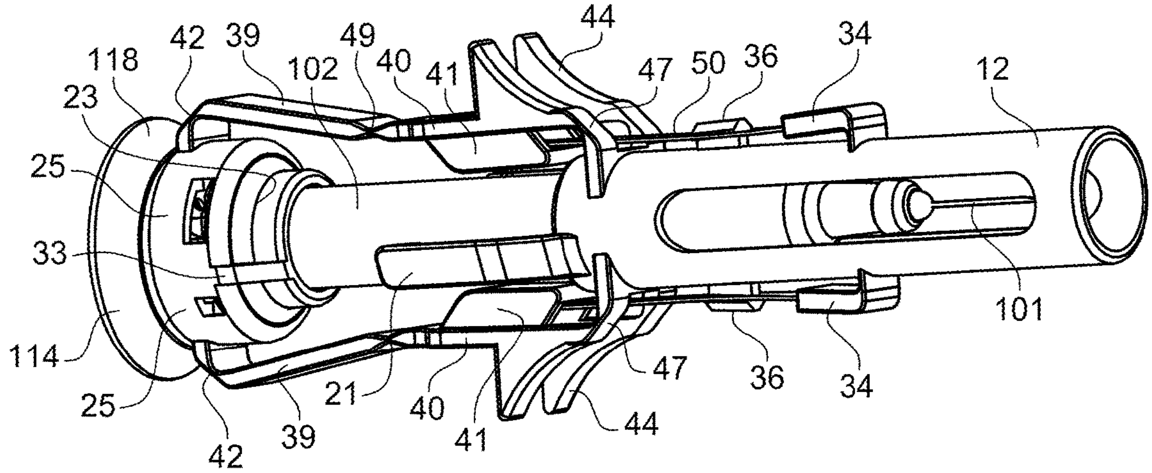
Figure 13:
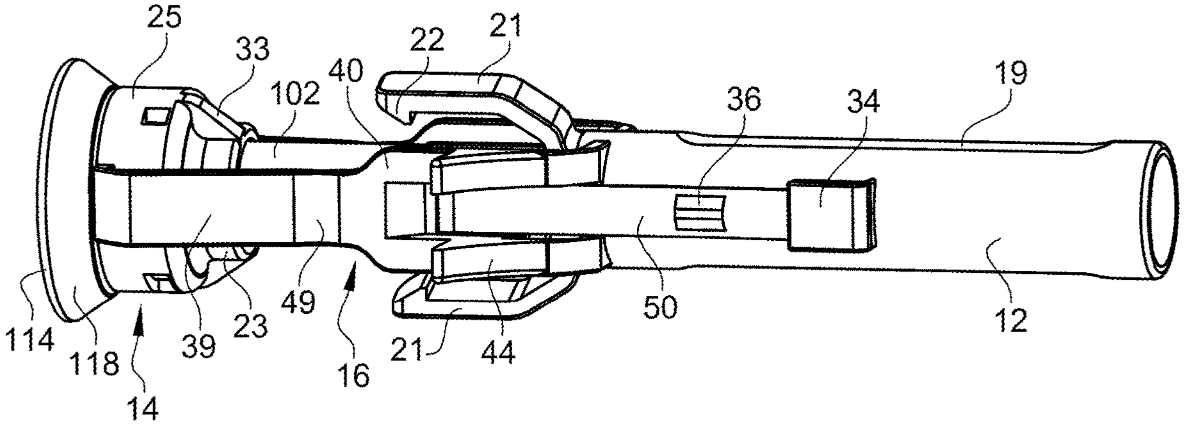

FIGS. 11 to 13 show the safety device 10 in the extended position where the spring blades 45 maintains the actuation arms 16.

FIG. 16 shows the safety device 10 in the extended position where the torsion springs 50 maintains the actuation arms 16.

FIG. 18 shows the safety device 10 in the extended position where the elastic band 55 maintains the actuation arms 16.

In some embodiments, the actuation arms 16 are in a state where the intermediate hinge 49 inwardly overtakes the plan defined by the proximal hinge 42 and distal hinge 47 as it can be best seen on FIG. 15. Thus, a force applied longitudinally on the tubular body 12 aiming at un-shielding the needle tip 101 cannot release the actuation arm 16 from its extended state. The tubular body 12 is maintained by the proximal link 39 and distal link 40 which being arranged as a toggle mechanism.

The protective device 10 accordingly achieves a substantially permanent locking of the tubular body 12 over the needle tip 101 without any input from the user as the mechanical energy stored in the biasing member 45 or 50 places the safety device 10 in an extended position where the needle is protected by the tubular body 12.

Figure 22:
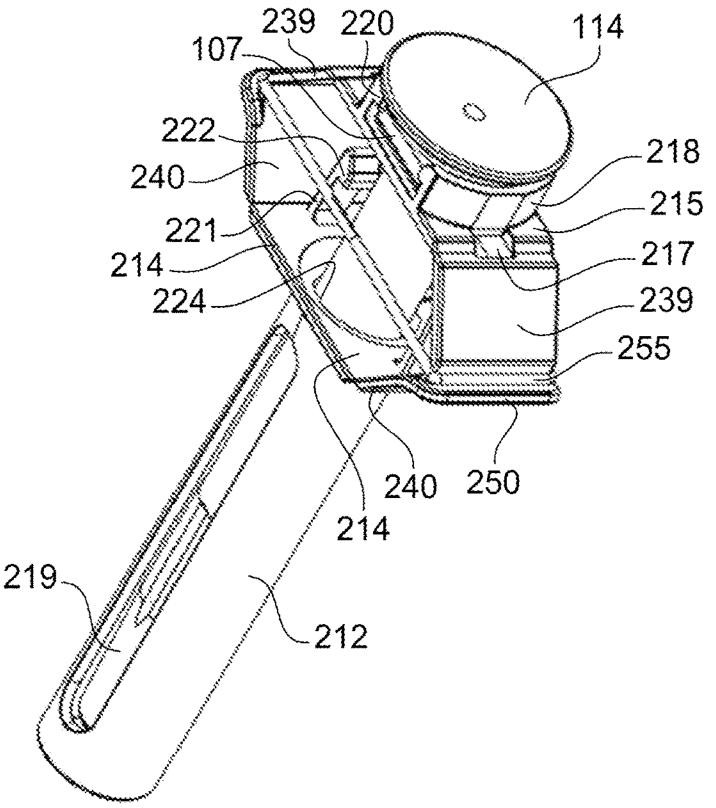
Figure 23:
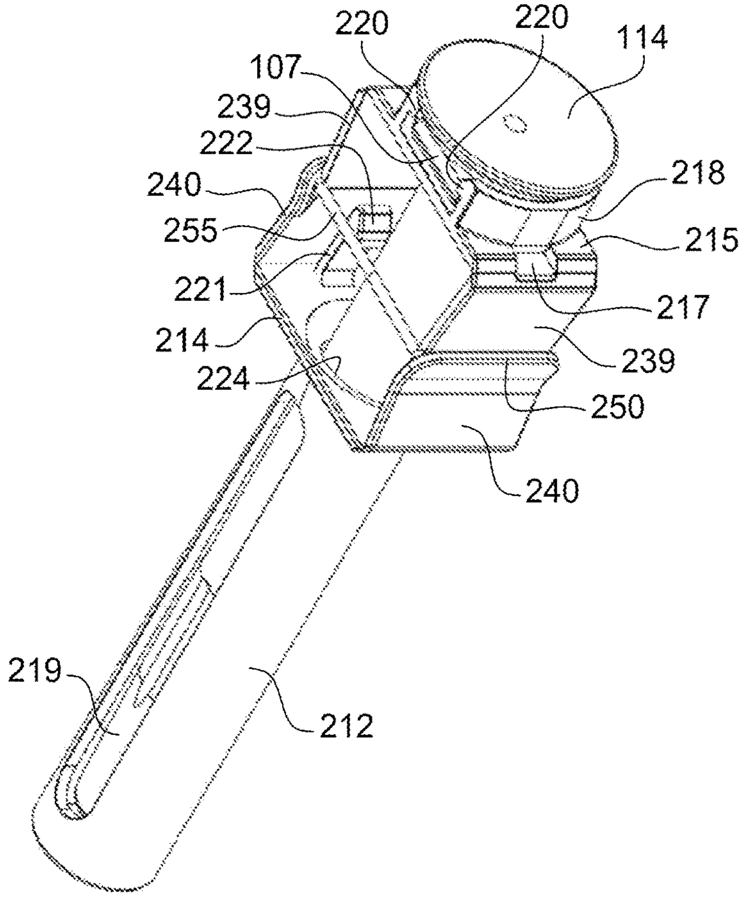

Turning to FIG. 19 to FIG. 23, the safety device 210 includes a tubular body 212, and is configured and sized to engage on the barrel 102 of a drug delivery device such as a prefilled syringe and a head arrangement which can include a crown 213 designed and configured to axially move between a locked collapsed position (FIG. 19) and a locked extended position (FIG. 23).

The tubular body 212 is a tubular element, which has an inner diameter sized and configured so that the tubular body 212 can axially slide relative to the barrel 102. In practice, the tubular body 212 inner diameter slightly exceeds the external diameter of the barrel 102. In some embodiments, the tubular body 212 can be provided with one or more windows 219 so that any marking or labelling applied on the barrel 102 and so that the drug contained in the barrel 102 can be visible to a user prior to injection. In the illustrated embodiments, the tubular body 212 is provided with two windows 219 spaced apart by 180°.

The crown 213 includes a distal plate 214 which is positioned at the proximal end of the tubular body 212. In the illustrated embodiment, the distal plate 214 has a quadrangular shape. As it can be seen on FIG. 22 and FIG. 23, the distal plate 214 includes two symmetrical legs 221. The legs 221 extend in cantilever from the distal plate 214 in the proximal direction. The cantilevered attachment of the legs 221 onto the distal plate 214 provides the legs 221 with elastic resilience in a radial direction relative to the tubular body 212. At the end of the legs 221, is a catch 222, which is internally oriented. In some embodiments, the catch 222 has a ramped end.

The crown 213 includes a proximal plate 215 which can have a quadrangular shape. On its proximal face, the proximal plate 215 is provided with locking elements where the flange 107 can engage the locking elements.

In some embodiments, the proximal plate 215 can include two symmetrical ribs 218. Each rib 218 can be provided with two cantilevered locking tooth 220.

The proximal plate 215 and the distal plate 214 are provided with two coaxial circular openings 223 and 224.

The proximal plate 215 can include two windows 217 which are each adjacent a ribs 218. The windows 217 are configured and sized to receive a leg 221. In other words, the legs 221 can engage the windows 217 and the catches 222 can lock onto the ribs 218 when the safety device 210 is in a collapsed position.

The crown 213 further includes two arms 216 which connect the distal plate 214 to the proximal plate 215. Each arm 216 includes a proximal link 239 and a distal link 240.

The proximal links 239 have a substantially rectangular shape and are each connected to proximal plate 215 by a first proximal hinge 242. In the illustrated embodiment, the first proximal hinges 242 are living hinges formed by a thinning of the plastic material, which the safety device 210 is made of. This allows the proximal links 239 to rotate relative to proximal plate 215.

The distal links 240 have a substantially rectangular shape and are each connected to the distal plate 214 by a distal hinge 247 which can be a living hinge made by a thinning of the plastic material which forms the safety device 10.

The proximal link 239 and the distal link 240 can be joined by an intermediate hinge 249, which can be a living hinge made by a thinning of the plastic material which forms the safety device 210.

Figure 20:
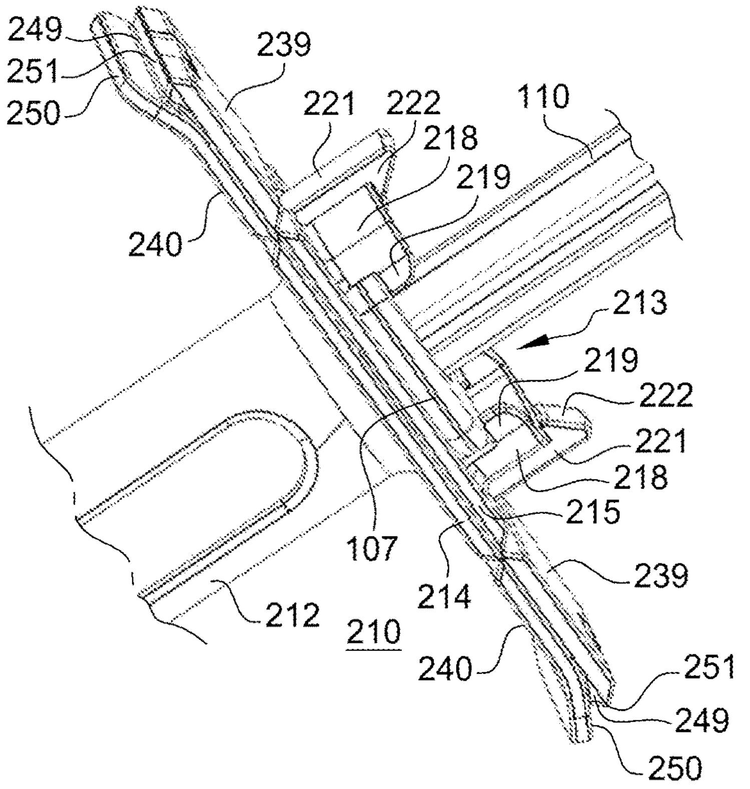
FIG. 20, FIG. 21, FIG. 22 and FIG. 23 show another embodiment of a safety device.
Figure 21:
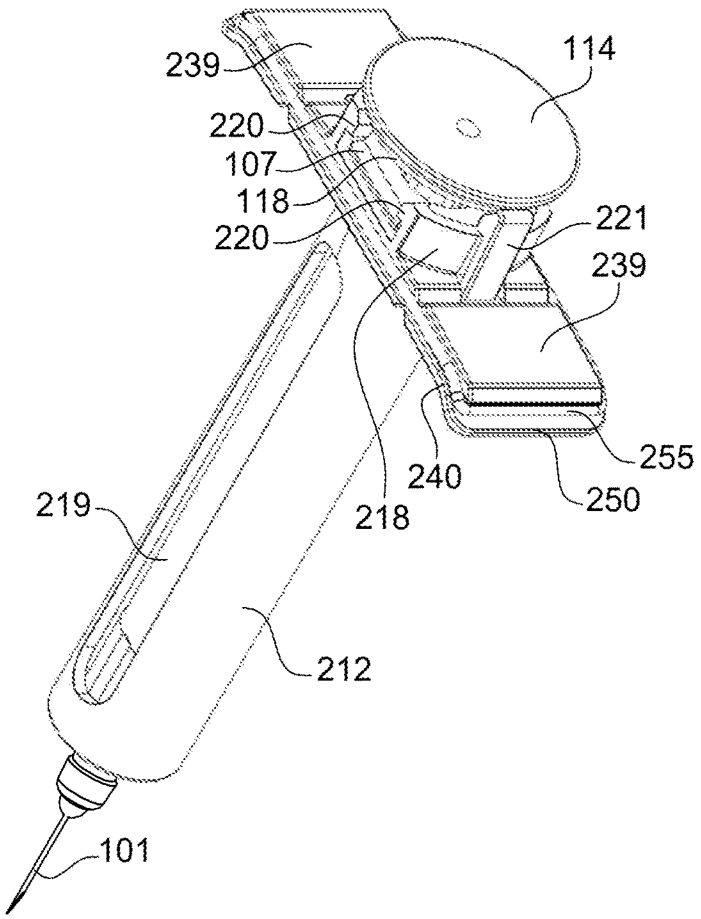

As it can be seen on FIG. 20 which depicts the safety device without a biasing member, the distal link 240 can include a lip 250 which is adjacent the intermediate hinge 249. Adjacent the intermediate hinge 249, the proximal link 239 includes a ramped end 251 which forms a groove with the lip 250. Said groove can be V shaped, U shaped or square shaped.

The actuation arms 216 are therefore transitionable between:

(i) a collapsed state where the proximal link 239 and the distal link 240 are substantially parallel to each other, or (ii) an extended state where the proximal link 239 and the distal link 240 form are substantially in line with each other.

In some embodiments, the safety device 210 can be a single piece component. Further, the safety device 210 can be formed by a single shot molding process.

The safety device 210 when in its initial state of FIGS. 19 to 23, has no internal capacity to move from the collapsed state to the extended state.

The safety device 210 of the invention includes at least one biasing member. The biasing member can be made of an elastic and resilient material, which has a low creep capability so that its resilience and its elasticity are maintained even after a long term storage.

In the embodiments of FIGS. 19 to 23, a biasing member which includes an elastic band 255 urges the actuation arms 216 toward their extended position. The elastic band 255 can be made of latex, rubber, silicone rubber, thermoplastics, thermoplastic elastomers, or other suitable elastic materials.

Figure 19:
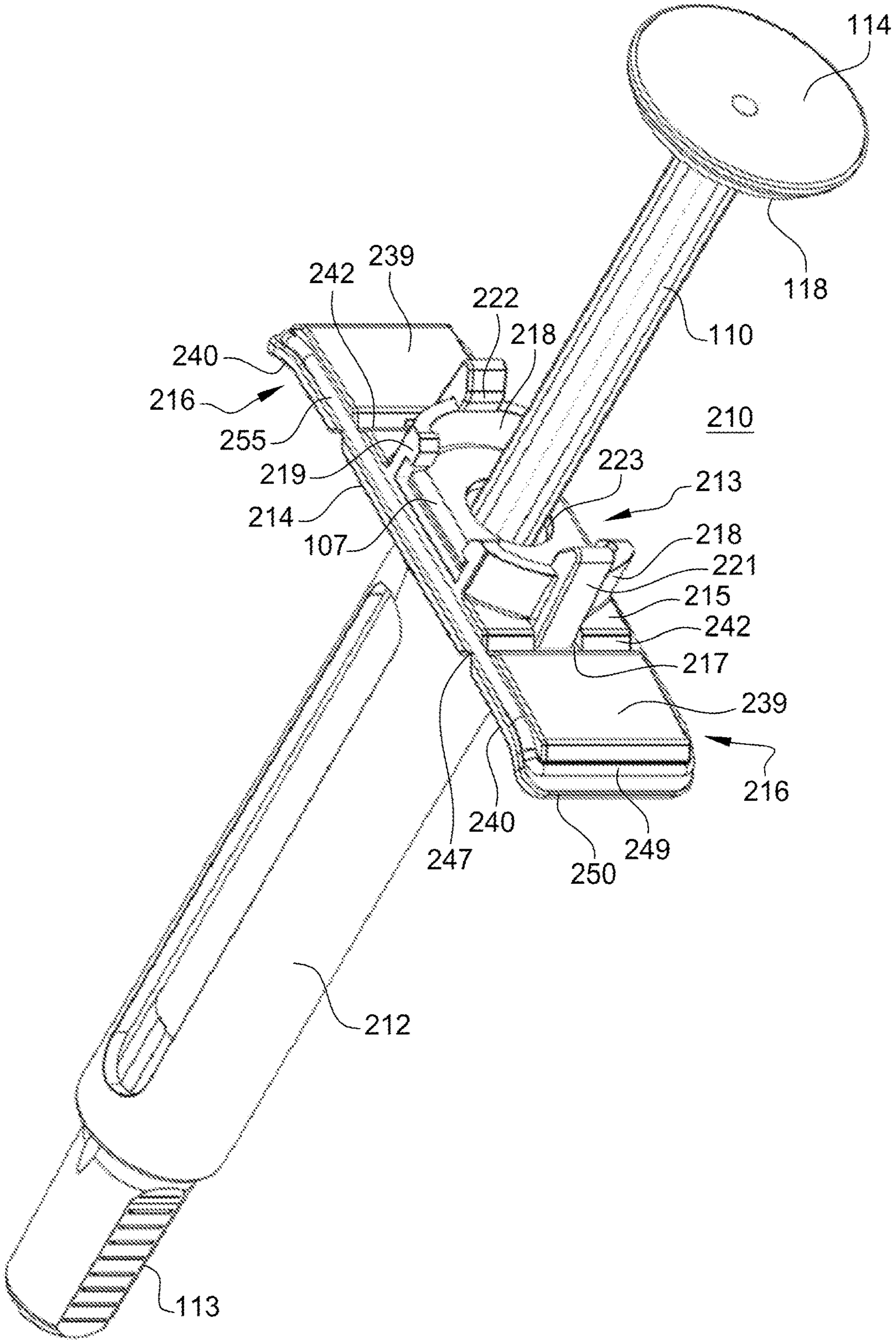
FIG. 19.

As it can be seen on FIG. 19 which shows the safety device in its collapsed position, the elastic band 255 stretches over the two actuation arms 216. The elastic band 255 is retained within the groove formed by the lip 250 and the ramped end 251 of the proximal link 239. The elastic band 255 is therefore in a stable position.

In its collapsed position shown on FIG. 19, the proximal link 239 and the distal link 240 are parallel and are maintained against each other by the legs 221 which engage the windows 217 and lock into the ribs 218.

FIG. 19 shows the safety device 210 fitted on a drug delivery device 100 which can be a prefilled syringe.

In this collapsed position, the crown 213 is locked onto the drug delivery device 100. To do so, the barrel flange 107 locks onto the ribs 108. The barrel flange 107 snaps fit onto the looking tooth 220.

The drug delivery device 100 is axially locked on the safety device 210, however the drug delivery device 100 is free to rotate relative to the safety device 10, which can be useful as user tend to rotate any drug delivery device before injection to visually check the drug which is about to be injected.

The drug delivery device fitted with a safety device 100 as illustrated on FIG. 19 can be stored for a later use.

When an injection of the drug contained in the drug delivery device 100 is required, a user may first remove the tip cap 113.

The drug delivery device 100 is ready for injection. The user can visually check the drug through the windows 219 and can rotate the plunder rod 110.

Administering an injection with a drug delivery device fitted with the safety device 210 is substantially the same as administering an injection with a drug delivery device fitted with the safety device 10 according to the prior art and thus is not likely to confuse a user and permits a user-friendly operation.

In an exemplary use illustrated on FIG. 19, the user can apply a pushing force on the piston rod flange 114 typically by applying a thumb on the piston rod flange 114 while the user maintains one finger—typically the index—on one distal link 240 and one finger—typically the middle finger—on the other distal link 240.

As the injection progresses, the piston rod flange 114 moves closer to the crown 213. At the end of the injection, the piston rod flange 114 abuts against the catches 222. By further pushing the piston rod flange 114, the ramp portion 118 comes in abutment with the ramp provided in the catch 222 of each legs 221 as indicated by the arrows of FIG. 20. The legs 221 are thus forced to deflect outwardly thereby releasing the catches 222 from the ribs 218. The actuation arms 216 and the tubular body 212 are released from the proximal plate 215 and are therefore free to move axially along the barrel 102.

The elastic band 255 exerts a force on the two opposite intermediate hinges 249 urging the proximal link 239 and the distal link 240 towards the extended position where the proximal link 239 and the distal link 240 are in line with each other as shown on FIG. 22.

In the extended position of the actuation arms 216, the tubular body 212 encapsulates the needle 101 as the tubular body 212 is pushed away from the proximal plate 215 which remains locked onto the flange 107.

In the extended position, the distal links 240 rest on the legs 221, this defining the final extended position.

The terminology used herein is for the purpose of describing particular aspects only and is not intended to be limiting of the disclosure. As used herein, the singular forms "a," "an," and "the" are intended to include the plural forms as well, unless the context clearly indicates otherwise. As used herein, the term "and/or" includes any and all combinations of one or more of the associated listed items. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

It will be understood that, although the terms first, second, etc., may be used herein to describe various elements, these elements should not be limited by these terms. These terms are only used to distinguish one element from another. For example, a first element could be termed a second element, and, similarly, a second element could be termed a first element without departing from the scope of the present disclosure.

Relative terms such as "below" or "above" or "upper" or "lower" or "horizontal" or "vertical" may be used herein to describe a relationship of one element to another element as illustrated in the Figures. It will be understood that these terms and those discussed above are intended to encompass different orientations of the device in addition to the orientation depicted in the Figures. It will be understood that when an element is referred to as being "connected" or "coupled" to another element, it can be directly connected or coupled to the other element, or intervening elements may be present. In contrast, when an element is referred to as being "directly connected" or "directly coupled" to another element, there are no intervening elements present.

Unless otherwise defined, all terms (including technical and scientific terms) used herein have the same meaning as commonly understood by one of ordinary skill in the art to which this disclosure belongs. It will be further understood that terms used herein should be interpreted as having a meaning consistent with their meaning in the context of this specification and the relevant art and will not be interpreted in an idealized or overly formal sense unless expressly so defined herein.

It is to be understood that the present disclosure is not limited to the aspects described above and illustrated in the drawings; rather, the skilled person will recognize that changes and modifications may be made within the scope of the appended claims.

The invention claimed is:

1. A safety device for mounting onto a drug delivery device having a barrel comprising a flange at its proximal end and an injection needle at its distal end, and a piston rod comprising a piston flange, the safety device comprising:

a tubular body extending along a longitudinal axis, the tubular body being configured to receive the barrel, a head arrangement configured to abut against the flange and to lock into the flange, at least two actuation arms connecting the tubular body and the head arrangement, the at least two actuation arms having a proximal link connected to the head arrangement by a proximal hinge and a distal link connected to the tubular body by a distal hinge, the proximal link and the distal link being connected by an intermediate hinge, the at least two actuation arms being movable between a collapsed position in which the tubular body is maintained in a position proximally close to the flange uncovering the needle and an extended position in which the tubular body is maintained in a position distally distant from the head arrangement shielding the needle;

a locking means for maintaining the at least two actuation arms in a collapsed position and a biasing member for maintaining the at least two actuation arms in an extended position;

wherein the biasing member comprises one distal end secured on the tubular body and one proximal end secured on the distal link.

2. The safety device of claim 1, wherein the biasing member is a member of the group consisting of a spring blade, a torsion spring and an elastic band.

3. The safety device of claim 2, wherein the spring blade has an opening.

4. The safety device of claim 2, wherein the torsion spring has a helical central part and two opposite ends.

5. The safety device of claim 1 wherein the head arrangement comprises an annular head which comprises a proximal ring and a distal ring jointed by a shoulder whereon the flange abuts.

6. The safety device of claim 5, wherein the tubular body comprises at least one leg, the at least one leg being the locking means and wherein the annular head comprises two ramp surfaces configured to guide the at least one leg when the at least one leg slide on the annular head.

7. The safety device of claim 1, wherein at least one of the hinges is a living hinge.

8. The safety device of claim 1, wherein the safety device is formed in a single shot injection molding process.

9. The safety device of claim 1, wherein the distal link comprises a housing configured to receive the biasing member proximal end and the tubular body comprises a casing configured to receive the biasing member distal end.

10. The safety device of claim 1, wherein the intermediate hinge inwardly overtakes a plane defined by the proximal hinge and distal hinge when the actuation arm is in its extended position.

11. The safety device of claim 1, wherein the head arrangement comprises an annular head, the annular head comprising at least one locking tab configured to axially retain the flange.

12. The safety device of claim 1, wherein the head arrangement comprises an annular head and wherein the tubular body comprises at least one leg, the at least one leg being the locking means, the at least one leg extending in cantilever and having a catch at its free end, the leg being configured to deflect radially outward to allow the catch to slide over the annular head during mounting and to deflect radially inward after mounting completion so that the catch axially retains the tubular body relative to annular head.

13. The safety device of claim 1, wherein at least one distal link comprises two longitudinal ribs having a proximal side perpendicular to the distal link and arcuate distal side.

14. The safety device of claim 1, wherein the tubular body comprises a means for securing the biasing member onto the tubular body.

15. A drug delivery device having a barrel comprising a flange at its proximal end and an injection needle at its distal end, and a piston rod comprising a piston flange fitted with a safety device according to claim 1, wherein the piston flange comprises a ramped surface distally convergent configured to outwardly deflect the locking means maintaining the actuation arms in a collapsed position.

16. A safety device for mounting onto a drug delivery device having a barrel comprising a flange at its proximal end and an injection needle at its distal end, and a piston rod comprising a piston flange, the safety device comprising:

a tubular body extending along a longitudinal axis, the tubular body being configured to receive the barrel, a head arrangement configured to abut against the flange and to lock into the flange, at least two actuation arms connecting the tubular body and the head arrangement, the at least two actuation arms having a proximal link connected to the head arrangement by a proximal hinge and a distal link connected to the tubular body by a distal hinge, the proximal link and the distal link being connected by an intermediate hinge, the at least two actuation arms being movable between a collapsed position in which the tubular body is maintained in a position proximally close to the flange uncovering the needle and an extended position in which the tubular body is maintained in a position distally distant from the head arrangement shielding the needle;

a locking means for maintaining the at least two actuation arms in a collapsed position and an elastic band for maintaining the at least two actuation arms in an extended position;

wherein the head arrangement comprises a crown having a proximal plate configured and sized to lock onto the flange and a distal plate mounted on the tubular body, the proximal plate and the distal plate being connected by at least two actuation arms.

17. The safety device of claim 16, wherein the proximal plate comprises two symmetrical ribs, each ribs having two locking teeth configured to retain the flange.

18. The safety device of claim 16, wherein the safety device comprises two legs having a catch, extending in cantilever from the distal plate, configured and sized to engage into a window provided in the proximal plate and to lock into the rib.

19. The safety device of claim 16, wherein the distal link comprises a lip adjacent the intermediate hinge and the proximal link comprises a ramped end adjacent the intermediate, which forms a groove with the lip.

20. A safety device for mounting onto a drug delivery device having a barrel comprising a flange at its proximal end and an injection needle at its distal end, and a piston rod comprising a piston flange, the safety device comprising:

a tubular body extending along a longitudinal axis, the tubular body being configured to receive the barrel, a head arrangement configured to abut against the flange and to lock into the flange, the head arrangement comprising an annular head which comprises a proximal ring and a distal ring jointed by a shoulder whereon the flange abuts;

at least two actuation arms connecting the tubular body and the head arrangement, the at least two actuation arms having a proximal link connected to the head arrangement by a proximal hinge and a distal link connected to the tubular body by a distal hinge, the proximal link and the distal link being connected by an intermediate hinge, the at least two actuation arms being movable between a collapsed position in which the tubular body is maintained in a position proximally close to the flange uncovering the needle and an extended position in which the tubular body is maintained in a position distally distant from the head arrangement shielding the needle;

a locking means for maintaining the at least two actuation arms in a collapsed position and a biasing member for maintaining the at least two actuation arms in an extended position;

wherein the tubular body comprises at least one leg, the at least one leg being the locking means and wherein the annular head comprises two ramp surfaces configured to guide the at least one leg when the at least one leg slide on the annular head.

* * * * *